United States Patent
Besser et al.

(10) Patent No.: US 10,376,447 B2
(45) Date of Patent: Aug. 13, 2019

(54) ENTERAL FEEDING SYSTEM WITH CONTROLLED REFLUX PREVENTIVE VACUUM SEALING

(71) Applicant: ENVIZION MEDICAL LTD., Tel Aviv (IL)

(72) Inventors: Doron Besser, Tel Aviv (IL); Guy Ben Ezra, Karkur (IL)

(73) Assignee: ENVIZION MEDICAL LTD., Tel Aviv (IL)

( * ) Notice: Subject to any disclaimer, the term of this patent is extended or adjusted under 35 U.S.C. 154(b) by 0 days.

(21) Appl. No.: 15/546,709

(22) PCT Filed: Feb. 2, 2016

(86) PCT No.: PCT/IL2016/050115
§ 371 (c)(1),
(2) Date: Jul. 27, 2017

(87) PCT Pub. No.: WO2016/125152
PCT Pub. Date: Aug. 11, 2016

(65) Prior Publication Data
US 2018/0049950 A1    Feb. 22, 2018

Related U.S. Application Data

(60) Provisional application No. 62/110,860, filed on Feb. 2, 2015.

(51) Int. Cl.
*A61J 15/00*    (2006.01)
*A61B 1/05*    (2006.01)
(Continued)

(52) U.S. Cl.
CPC ............ *A61J 15/0015* (2013.01); *A61B 1/00* (2013.01); *A61B 1/05* (2013.01); *A61B 1/0676* (2013.01);
(Continued)

(58) Field of Classification Search
CPC .. A61J 15/0015; A61J 15/003; A61J 15/0073; A61J 15/0076; A61J 15/0069;
(Continued)

(56) References Cited

U.S. PATENT DOCUMENTS 4,904,238 A    2/1990  Williams
4,968,307 A *  11/1990 Dake .................. A61M 25/007
                                                    604/264

(Continued)

FOREIGN PATENT DOCUMENTS

EP          2301512        3/2011
WO        2003034976       5/2003
(Continued)

*Primary Examiner* — Nathan R Price
*Assistant Examiner* — Mark Alan Igel
(74) *Attorney, Agent, or Firm* — The Roy Gross Law Firm, LLC; Roy Gross

(57) ABSTRACT

An enteral feeding system including: an enteral feeding tube, a pump configured to draw a liquid from a reservoir to the enteral feeding tube; a switching mechanism associated with at least four vacuum lumens provided with the enteral feeding tube; and a controller configured to automatically control the pump and the switching mechanism wherein controlling the pump and the switching mechanism includes coordinating the operation of the switch with the operation of the pump.

16 Claims, 9 Drawing Sheets

(51) Int. Cl.
  *A61B 1/00* (2006.01)
  *A61B 1/06* (2006.01)
  *A61B 5/00* (2006.01)
  *A61B 1/233* (2006.01)
  *A61B 1/273* (2006.01)
  *A61M 5/142* (2006.01)
  *A61B 5/01* (2006.01)

(52) U.S. Cl.
  CPC ............ *A61B 1/0684* (2013.01); *A61B 1/233* (2013.01); *A61B 1/2736* (2013.01); *A61B 5/4233* (2013.01); *A61B 5/4238* (2013.01); *A61J 15/0069* (2013.01); *A61J 15/0073* (2013.01); *A61J 15/0076* (2015.05); *A61M 5/142* (2013.01); *A61B 5/0066* (2013.01); *A61B 5/01* (2013.01)

(58) Field of Classification Search
  CPC ........ A61M 16/0463; A61B 1/00; A61B 1/05; A61B 1/0676; A61B 1/0684; A61B 1/233; A61B 1/2736; A61B 5/4233; A61B 5/4238; A61B 5/142
  See application file for complete search history.

(56) References Cited

U.S. PATENT DOCUMENTS

| | | | |
|---|---|---|---|
| 5,389,074 A | 2/1995 | Parker et al. | |
| 5,707,351 A | 1/1998 | Dorsey, III | |
| 6,126,647 A | 10/2000 | Posey et al. | |
| 6,165,164 A | 12/2000 | Hill et al. | |
| 6,695,764 B2 * | 2/2004 | Silverman | A61F 2/04 600/29 |
| 6,790,214 B2 * | 9/2004 | Kraemer | A61B 17/0644 606/142 |
| 7,794,425 B2 | 9/2010 | Gobel | |
| 7,967,780 B2 | 6/2011 | Goebel | |
| 8,100,874 B1 | 1/2012 | Jordan et al. | |
| 8,453,648 B2 | 6/2013 | Black et al. | |
| 2003/0208209 A1 * | 11/2003 | Gambale | A61B 17/00234 606/144 |
| 2004/0082909 A1 * | 4/2004 | Shia | A61M 39/12 604/77 |
| 2004/0153098 A1 | 8/2004 | Chin et al. | |
| 2004/0220515 A1 * | 11/2004 | Constantz | A61M 25/0032 604/43 |
| 2005/0059962 A1 | 3/2005 | Phan et al. | |
| 2005/0137574 A1 | 6/2005 | Sakal et al. | |
| 2008/0077043 A1 | 3/2008 | Malbrain et al. | |
| 2008/0195047 A1 * | 8/2008 | Price | A61J 15/0015 604/151 |
| 2009/0069796 A1 * | 3/2009 | Oskin | A61B 18/04 606/27 |
| 2009/0306626 A1 | 12/2009 | Sinha et al. | |
| 2009/0317760 A1 | 12/2009 | Gadbois | |
| 2010/0030133 A1 * | 2/2010 | Elia | A61B 5/037 604/28 |
| 2011/0046653 A1 | 2/2011 | Addington et al. | |
| 2011/0130650 A1 | 6/2011 | Dayan et al. | |
| 2012/0150111 A1 * | 6/2012 | Hershey | A61M 39/08 604/122 |
| 2013/0158471 A1 * | 6/2013 | Neel | A61M 1/0084 604/35 |
| 2013/0310806 A1 * | 11/2013 | Nevler | A61J 15/003 604/516 |
| 2014/0066880 A1 * | 3/2014 | Prince | A61M 5/16881 604/500 |
| 2014/0088359 A1 | 3/2014 | Quale | |
| 2014/0100531 A1 * | 4/2014 | Ankrum | A61M 1/0084 604/181 |
| 2014/0188080 A1 | 7/2014 | Besser et al. | |
| 2014/0235960 A1 | 8/2014 | Addington et al. | |
| 2015/0174013 A1 | 6/2015 | Besser et al. | |

FOREIGN PATENT DOCUMENTS

| | | |
|---|---|---|
| WO | 2007095541 | 8/2007 |
| WO | 2015198297 | 12/2015 |
| WO | 2016024260 | 2/2016 |

* cited by examiner

ENTERAL FEEDING SYSTEM WITH CONTROLLED REFLUX PREVENTIVE VACUUM SEALING

This application is a 35 U.S.C. § 371 national phase application PCT/IL2016/050115 filed Feb. 2, 2016, which claims priority to U.S. Provisional Patent Application No. 62/110,860 filed Feb. 2, 2015. Both applications are incorporated herein by reference as if fully set forth.

FIELD OF THE INVENTION

The present invention relates to feeding pumps.

BACKGROUND OF THE INVENTION

Enteral feeding is a form of hyperalimentation and metabolic support in which nutrient formulas or medicaments are delivered directly to the GI tract, either to the stomach or the duodenum. A nasogastric tube (NGT) is used for feeding and administering drugs and other oral agents. The tube is inserted into the patient's esophagus and stomach in order to ensure the passage of the agents into the stomach and not into the lungs. The NGT can also be used for suction of fluids from the stomach.

However, the use of NGTs can have disadvantages. Minor complications include nose bleeds, sinusitis, and a sore throat. Sometimes more significant complications occur including erosion of the nose where the tube is anchored, esophageal perforation, pulmonary aspiration, a collapsed lung, or intracranial placement of the tube.

Even worse, during feeding, excessive gastric pressure may result. From time to time, the body relieves such excess gastric pressure by expelling gas or liquid or reflux fluid. The fluids are expelled from the stomach through the esophagus to the mouth or nasal pathways. The reflux fluids may be inhaled into the lungs with possible risk of aspiration pneumonia, bacterial infection in the pharynx or esophagus or any other ailments. Accordingly, numerous studies have linked the use of the NGT to an increase in ventilator-associated pneumonia (VAP). VAP is the most common nosocomial infection in the intensive care unit (ICU), and it is associated with prolonged hospitalization, increased health care costs, and high attributable mortality.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

There is provided, in accordance with an embodiment, a nasogastric apparatus, comprising: a pump configured to draw a liquid from a reservoir to a nasogastric tube; a switching mechanism associated with at least two vacuum lumens provided with the nasogastric tube; and a controller configured to control the pump and the switching mechanism.

In some embodiments, the liquid comprises food.

In some embodiments, the liquid comprises medicine.

In some embodiments, the switching mechanism comprises one or more valves, and wherein the controller is configured to control the switching mechanism by selecting to activate or deactivate any of the one or more valves.

In some embodiments, the one or more valves are selected from the group consisting of: a pinch valve, a butterfly valve, and a diaphragm valve.

In some embodiments, each of the at least two vacuum lumens is associated with a different valve of the one or more valves.

In some embodiments, each valve of the one or more valves is associated with a set of vacuum lumens that are disposed with one or more sealing portions at a specific longitudinal location along the nasogastric tube.

In some embodiments, the controller is configured to control a location of a sealing of the esophagus against the nasogastric tube by selecting to activate a valve associated with the location.

In some embodiments, the controller is configured to alternately activate a suction at a distal location and a proximal location of the nasogastric tube.

In some embodiments, the controller is further configured to control a gastric decompression lumen provided with the nasogastric tube via a gastric decompression valve provided with the switching mechanism.

In some embodiments, the gastric decompression lumen is configured to siphon a fluid from a stomach of a patient to a reservoir coupled to the decompression lumen via the switching mechanism.

In some embodiments, the switching mechanism is configured to provide a control point for releasing suction from any of the at least two vacuum lumens.

In some embodiments, the controller is configured to control a safety valve provided between a vacuum source and switching mechanism, thereby controlling any suction applied to any of the at least two vacuum lumens.

In some embodiments, the controller is configured to control the switching mechanism to regulate the suction within any of the two or more vacuum lumens to an oscillatory movement of the esophagus.

In some embodiments, the oscillatory movement is a peristaltic movement.

In some embodiments, the apparatus further comprises a user interface to enable a practitioner to set one or more parameters for controlling the application of a suction to any of the two or more lumens via the controller and switching mechanism.

In some embodiments, the apparatus further comprises a user interface to enable: a patient to set a subset of the one or more parameters.

There is provided, in accordance with an embodiment, a method for enteral feeding, comprising: controlling an operation of a pump to draw a liquid from a reservoir to a nasogastric tube that is inserted into an esophagus of a patient; and controlling an operation of a switch associated with at least two vacuum lumens provided with the nasogastric tube, thereby providing the liquid to the patient's stomach via the nasogastric tube, while providing a vacuum to the vacuum lumens that seal the wall of the esophagus to the vacuum lumens.

In some embodiments, the method further comprises synchronizing the operation of the switch with the operation of the pump.

In some embodiments, the method further comprises decompressing the patient's stomach or intestine via a gastric decompression lumen provided with the nasogastric tube.

In addition to the exemplary aspects and embodiments described above, further aspects and embodiments will become apparent by reference to the figures and by study of the following detailed description.

BRIEF DESCRIPTION OF THE DRAWINGS

The present invention will be understood and appreciated more fully from the following detailed description taken in conjunction with the drawings in which.

DETAILED DESCRIPTION

A nasogastric apparatus is disclosed herein, which apparatus is configured to operate in conjunction with a nasogastric tube ("NGT") equipped with vacuum lumens that aid in the sealing of the esophagus of a patient to prevent reflux and/or the like. The apparatus may include a pump for drawing liquid food and/or liquid medication from a reservoir towards the nasogastric tube; a switching mechanism associated with at least two of the vacuum lumens; and a controller configured to control the operation of the pump and to control the operation of the switching mechanism, so as to provide the liquid food and/or liquid medication to the patient's stomach via the nasogastric tube, while providing a vacuum to the vacuum lumens that form a partial or complete seal between the wall of the esophagus and the circumference of the nasogastric tube.

The controller, optionally, may synchronize the operation of the switch, and thus the vacuum supplied to the NGT, with the operation of the pump. For example, the controller may time the vacuum to operate during feeding to seal the NGT within the esophagus, and prevent reflux. Additionally, the control unit may automatically alternate and time the operation of different pairs of vacuum lumens provided with the NGT to prevent necrosis over prolonged periods of use.

According to some embodiments, the NGT is configured to perform as a feeding tube as well as a gastric decompression tube and enable the controlled administration of nutrients and/or drugs directly to a subject's stomach or intestines and simultaneously or interchangeably control gastric decompression.

Figure 1A:
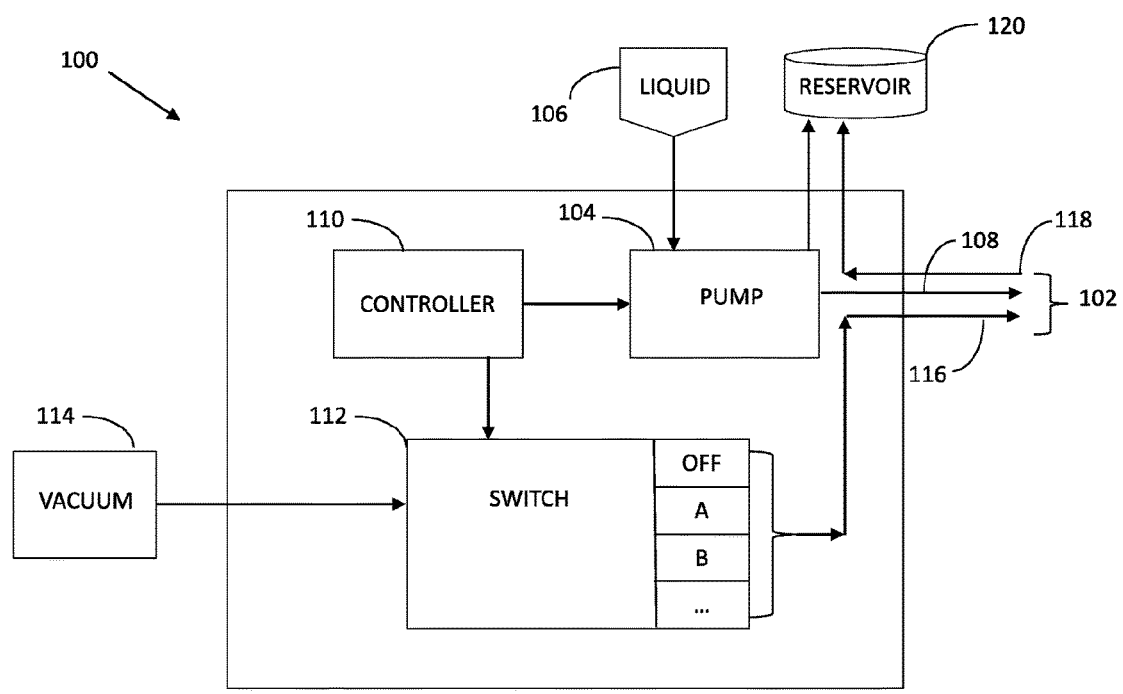
FIG. 1A illustrates a block-flow diagram of a nasogastric feeding apparatus in accordance with an embodiment of the invention.

Reference is now made to FIG. 1A which illustrates a block-flow diagram of a nasogastric feeding apparatus 100 that is configured to operate with a nasogastric (NGT) device 102. Apparatus 100 may include a pump 104 that is configured to draw a liquid, such as food and/or medicine, from a receptacle 106 towards a central tube 108, that is provided with NGT 102 to deliver the liquid to a patient. Apparatus 100 may further include a controller 110 that is configured to control pump 104 and to additionally control a vacuum switch 112 that connects a vacuum source 114, such as a central vacuum source that is typically available at hospitals for supplying a suction, to multiple sets of vacuum lumens 116 provided with the NGT 102, and which will be described in greater detail below.

In one embodiment, a vacuum control unit may be provided to control the coupling of the esophagus to NGT 102 to disable any reflux of liquid from the stomach to the esophagus and trachea. Thus, the location of the esophagus coupling to the tube may be changed in time, and controlled by apparatus 100 to diminish tissue damage to the esophagus, as follows:

Switch 112 may be configured to adjust a level and/or timing of the suction supplied to lumens 116, such as by operating one or more valves (not shown) provided with switch 112 in response to a signal from controller 110. The valves may comprise any known mechanism for controlling flow within the lumens, such as a pinch valve, diaphragm valve, or butterfly valve, to name a few.

In one embodiment, controller 108 may control the suction applied to any of lumens 116 by activating the following settings of switch 112:

setting switch 112 to the 'OFF' position may activate the valves within lumens 116 thereby sealing the lumens 116, removing the suction therein, and which may be useful for inserting and removing NGT 102 from a patient;

setting the 'A' position may deactivate a first set of valves corresponding to a first set of vacuum lumens, and which opens the first set of valves to supply the suction to the first set of vacuum lumens and seal a first region of the esophagus associated with the first set of vacuum lumens. Simultaneously, a second set of valves corresponding to a second set of vacuum lumens are activated, which closes the second set of valves to remove the suction from the second set of vacuum lumens and release, or detach from the second set of lumens a second region of the esophagus associated with the second set of lumens;

setting the 'B' position may deactivate the second set of valves corresponding to the second set of vacuum lumens, and which opens the second set of valves to supply the suction to the second set of vacuum lumens and seal a second region of the esophagus associated with the second set of lumens. Simultaneously, the first set of valves corresponding to the first set of vacuum lumens are activating, which closes the first set of valves to remove the suction from the first set of vacuum lumens and release, or detach from the first set of lumens the first region of the esophagus associated with the first set of lumens.

Table 1 below illustrates an exemplary set of operation modes for multiple sets of valves configured with switch 112 to control the suction applied to vacuum lumens 116. Although Table 1 refers to two sets of valves, a distal set and a proximal set, the system may employ additional sets of valves.

TABLE 1

| | valve operation modes | | | |
|---|---|---|---|---|
| | Distal suction | Distal release | Proximal suction | Proximal release |
| NGT insertion | − | + | − | + |
| Distal aspiration activate | + | − | − | − |

TABLE 1-continued valve operation modes

|  | Distal suction | Distal release | Proximal suction | Proximal release |
|---|---|---|---|---|
| Distal Aspiration deactivate | − | + | − | − |
| Proximal aspiration activate | − | − | + | − |
| Proximal Aspiration deactivate | − | − | − | + |
| NGT removal | − | + | − | + |

Controller 110 may signal switch 112 to control the valves as follows:
- when the NGT is inserted or removed from the patient, the distal and proximal valves are activated to block and suction from the vacuum lumens, and release the esophagus from the NGT at both the distal and proximal position.
- To activate aspiration, or suction, at the distal region (i.e. region 'A' above), the set of distally positioned valves is deactivated, thereby applying the suction to the corresponding vacuum lumens and attaching the esophagus to the vacuum lumens at the distal region.
- To deactivate aspiration, or suction, at the distal region, the set of distally positioned valves is activated, thereby blocking the suction from the corresponding vacuum lumens and releasing the esophagus from the vacuum lumens at the distal region.
- To activate aspiration, or suction, at the proximal region (i.e. region 'B' above), the set of proximally positioned valves is deactivated, thereby applying the suction to the corresponding vacuum lumens and attaching the esophagus to the vacuum lumens at the proximal region.
- To deactivate aspiration, or suction, at the proximal region, the set of proximally positioned valves is activated, thereby blocking the suction from the corresponding vacuum lumens and releasing the esophagus from the vacuum lumens at the proximal region.

In one embodiment, controller 110 may control a safety valve provided between vacuum source 114 and switch 112, and thus control any suction applied to lumens 116.

In one embodiment, controller 110 may alternately apply and remove the suction from vacuum lumens 116 at predetermined time intervals, such as by setting and unsetting the 'OFF' position of switch 112. In another embodiment, controller 110 may alternate between setting and unsetting the 'A' and 'B positions of switch 112, to alternately seal and release the first and second regions of the esophagus to the lumens, such as at predetermined time durations. In this manner, tissue damage to the esophagus, such as necrosis, may be prevented. In one embodiment, the time duration may be an hour. In another embodiment the time duration may be 30 minutes.

In one embodiment, controller 110 may prevent pump 104 from providing a liquid to main lumen 108 unless at least one region of the esophagus is sealed to NGT 102 via any suction applied to any of vacuum lumens 116, such as if any of position 'A' or position 'B' of switch 112 is set.

In one embodiment, controller 110 may control switch 112 to apply suction to any of vacuum lumens 116 for a predetermined time period, such as 2 hours, after pump 104 has finished a delivering food and/or medicine via main lumen 108, thereby sealing the esophagus to the NGT device to prevent reflux.

In one embodiment, controller 110 may set switch 112 to direct a flow within a gastric decompression lumen 118 provided with NGT 102 by activating a gastric decompression valve provided with switch 112. Gastric decompression lumen 118 may be coupled, via switch 112, to a reservoir 118 that is configured to collect a fluid, such as gastric gas, or excessive reflux, drawn by decompression lumen 116 from a stomach of the patient. The decompression lumen may be configured to decompress the patient's abdomen, including but not limited to the stomach or intestines.

In one embodiment, switch may be further configured to provide a control point for releasing suction from an inactive vacuum lumen and detach it from the esophagus.

Controller 110 may allow a care provider to set one or more parameters to control the application of a suction to any of lumens 116 prior to, during or after a patient is being fed by the NGT described herein, such as via a user interface. In additional embodiments, controller 110 may allow a patient to set a subset of parameters, such as to control the decompression ports to relieve abdominal discomfort.

Figure 1B:
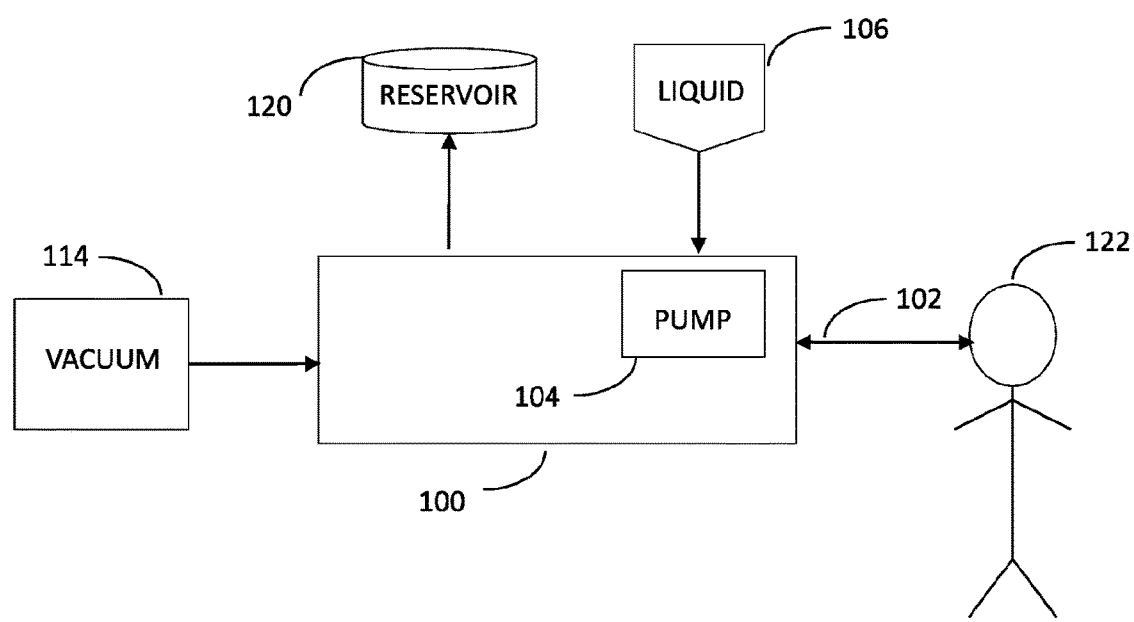
FIG. 1B illustrates another view of the system of FIG. 1A.

Reference is made to FIG. 1B which illustrates another view of the system of FIG. 1A. Nasogastric feeding apparatus 100 may function as an intermediary to control and coordinate any suction supplied from vacuum source 114 and flow of liquid from pump 104 through apparatus 100 to a patient 122. Additionally, apparatus 100 may control the flow through the decompression lumen from patient 122 to reservoir 120 and coordinate it with the operation of the other lumens included with apparatus 100.

NGT 102 may be used in ICU, or elsewhere, in order to reduce the complications associated with reflux such as the risk of VAP and in order to prevent or reduce tissue damage. In one embodiment, the NGT 102 may comprise at least one main lumen configured to provide a liquid from reservoir 106 to the stomach of a patient, and one or more peripheral lumens. In one embodiment, at least one suction port is provided to aspirate fluids from the esophagus and to sealingly draw an inner wall of the esophagus thereagainst interchangeably or simultaneously.

In some embodiments, a tube according to the present invention may be used in other locations in the GI tract or in any other body lumen, such as arteries, veins, etc. However, for simplicity of discussion, this tube is referred to throughout the specification as an NGT.

In some embodiments, NGT 102 includes a main lumen for providing a liquid to the patient, one or more vacuum lumens configured to sealingly draw an inner wall of an esophagus towards and against the outer contour of NGT 102 and optionally aspirate fluids from the esophagus, and a lumen configured to perform gastric decompression. Each lumen may be provided with one or more valves that are operable by controller 110 via switch 112 to control any flow or suction therein. By controlling the suction within the lumens of NGT 102 via the valves and switch 112, controller 110 may control either simultaneous vacuum pressure in one or more vacuum lumens of NGT 102 or changeable vacuum pressure between the different suction units.

In this way, controller 110 and switch 112 may operate NGT 102 to prevent reflux and aspiration of substances or liquids into the patient's lungs and prevents tissue damage, while obviating the need to remove and replace the entire device from the patient's esophagus.

Figure 2A:
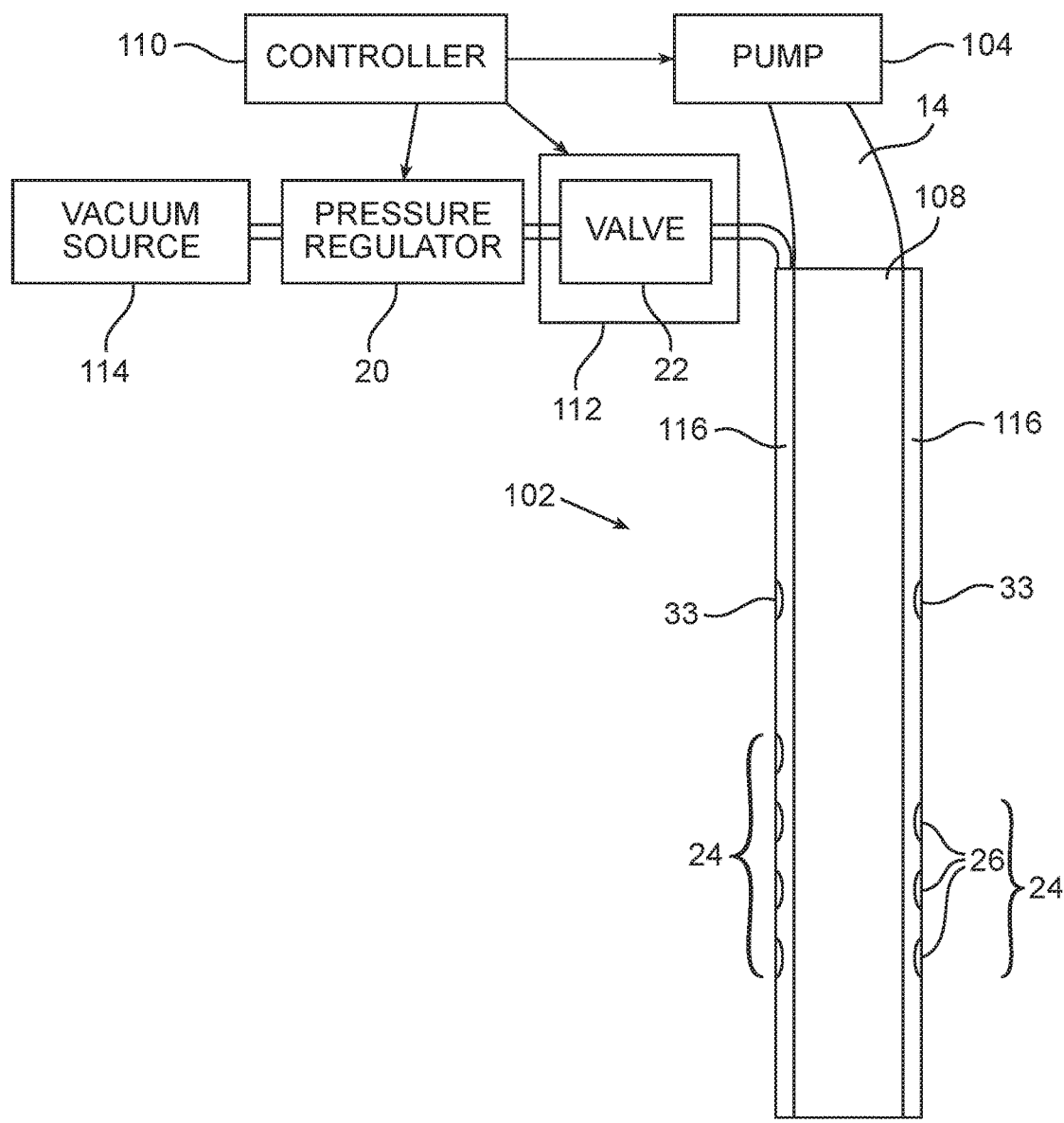
FIGS. 2A-B, illustrates a detailed view of a nasogastric tube, in accordance with an embodiment of the invention.
Figure 2B:
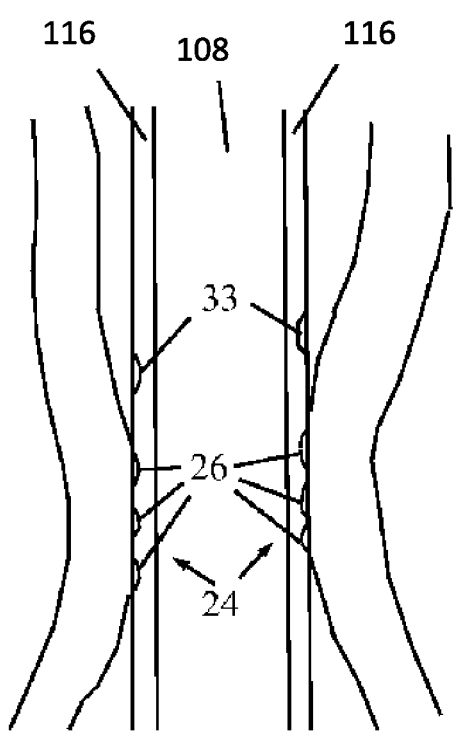

Reference is now made to FIGS. 2A-B, which illustrate a detailed view of NGT 102, in accordance with an embodiment. NGT 102 may include main lumen 108 coupled to pump 104 via one or more proximal connectors 14 and thus may provide a liquid to the stomach, or siphon a liquid from the stomach. Main lumen 108 may comprise multiple lumens, such as a lumen for providing food or medication to the patient and another lumen for siphoning liquid from the patient, each connected to pump 104 via a different connector 14. Controller 110 may control the operation of pump 104 and thus control the flow of any liquids within main lumen 108.

NGT 102 may include one or more vacuum lumens 116 peripherally surrounding main lumen 108. The term "peripherally surround" as used in the description and claims, encompasses continuous surrounding (no gaps between the vacuum lumens or one continuous, peripheral vacuum lumen) and discontinuous surrounding (wherein there are separations between discrete vacuum lumens).

Vacuum lumens 116 may be coupled with vacuum source 114 via switch 112 and controlled by controller 110, as described above. A pressure regulator 20 may be provided to regulate the vacuum pressure supplied by vacuum source 114. In one embodiment, controller 110 may control the operation of regulator 20.

Pressure regulator 20 may match the vacuum level generated by vacuum source 114 to the suction required in vacuum sealing portion 24. Such vacuum pressure may be, for example, between 0.5-50, 50-100, 100-200, 200-300, 300-400, 400-500, 500-600 or 600-700 mmHg. Different vacuum pressure values may be suitable to different patients and/or to different luminal structures into which the tube of the present invention is inserted.

In one embodiment, at least two sets vacuum lumens 116 peripherally surround main lumen 108. Vacuum lumens 116 may be equally or unequally spaced from each other. Main lumen 108 and vacuum lumens 116 are thus arranged as concentrically arranged conduits.

Main lumen 108 may be constructed from any suitable biocompatible material, such as but not limited to, polyurethane, silicone, polyvinyl chloride and many others. The vacuum lumens 16 may be constructed of similar materials, but alternatively may be constructed of medically safe metals, such as but not limited to, stainless steel, titanium alloys, NITINOL and others. Generally, without limitation, main lumen 108 may have a length in the range of 50 to 130 cm, with an outside diameter in the range of 5-12 Fr.

Main lumen 108 and vacuum lumens 116 may be constructed as one unit. Alternatively, vacuum lumens 116 may form a separate unit which is slid over main lumen 108 after insertion of main lumen 108 into the patient body. As another alternative, vacuum lumens 116 may be first introduced into the patient, and main lumen 108 may be slid in between vacuum lumens 116. Each of vacuum lumens 116 may include a vacuum sealing portion 24, which includes one or more suction ports 26, where some vacuum lumens may have more suction ports than others.

Referring to FIG. 2B, upon application of vacuum generated by vacuum source 114, the inner wall of the esophagus is drawn by negative pressure towards and against suction ports 26 (the outer contour of NGT 102). The outer contour of NGT 102, at least at vacuum sealing portion 24, is preferably round (circular or oval), for better conforming to and sealing of the esophagus.

In one embodiment, the vacuum sealing restricts at least 15% of the passage through the esophagus. In one embodiment, the vacuum sealing restricts at least 40% of the passage through the esophagus. In one embodiment, the vacuum sealing restricts at least 50% of the passage through the esophagus. In one embodiment, the vacuum sealing restricts at least 60% of the passage through the esophagus.

In one embodiment, the vacuum sealing restricts between 15 to 85% of the passage through the esophagus. In one embodiment, the vacuum sealing restricts between 30 to 80% of the passage through the esophagus. In one embodiment, the vacuum sealing restricts between 40 to 60% of the passage through the esophagus.

Controller 110 may supply vacuum pressure to gastric decompression lumen may in proportion to the amount of gas and/or excessive reflux being siphoned, and may apply either a constant or pulsed vacuum pressure. Valve 22, controllable by controller 110 via switch 112, may provide variability to the applied vacuum pressure to any of vacuum lumens 116.

Controller 110 may signal switch 112 to activate valve 22 to shift the vacuum between the different vacuum lumens 116 so that the suction level is not constant over time in the vacuum sealing portion 24, which may provide variability in how the esophagus wall is sucked in, and for how long.

NGT 102 may be provided with different numbers of vacuum sealing portions 24 and suction ports 26, and the vacuum to the sealing portions 24 may be regulated by controller 110 and switch 112 to create peristaltic movement or other oscillatory movement of the esophagus.

In accordance with an embodiment of the invention, controller 110 and switch 112 may control any of the following: one or more auxiliary suction ports 33 may be provided proximal to vacuum sealing portion 24. Since vacuum sealing portion 24 seals off the esophagus, any oropharyngeal secretions, such as saliva, may accumulate above (i.e., proximal to) vacuum sealing portion 24. Auxiliary suction ports 33 may be used to suck and remove such secretions. Additionally or alternatively, one or more of vacuum lumens 116 may be used to evacuate liquids arriving from the patient's stomach. That is, if a reflux occurs, one or more of vacuum lumens 116 may withdrawn at least a portion of it, through suction ports 26, towards valve 22. There, the stomach contents may be collected at reservoir 120 and then discarded.

In some embodiments, the suction ports of vacuum lumens 116 may be distributed along a longitudinal axis of NGT 102 and decompression port(s) 23 may be located at a distal end of NGT 102 in a manner to be positioned inside the stomach or duodenum of the patient. The suction ports of vacuum lumens 116 may be peripherally distributed around main lumen 108 in the same longitudinal location with respect to main lumen 108. In this configuration, controller 110, via switch 112, can control the sealing of the esophagus against NGT 102 in different peripheral locations, by selecting to activate and/or deactivate the valves provided with vacuum lumens 116.

In one embodiment, controller 110, via switch 112 and the associated valves, may control the suction to selected vacuum lumens 116. For example, to provide maximal sealing of the esophagus, controller 110 may provide a suction to all vacuum lumens 116 simultaneously. Alternatively, controller 110 may provide a suction to any combination of lumens 116 corresponding to different peripheral locations with respect to main lumen 108 and in at different longitudinal location along NGT 102. Controller 110 may additionally control the timing of any applied suction to any of lumens 116, and coordinate the applied suction with the operation of pump 104, as described above.

Switching the applied vacuum between the vacuum lumens allows applying vacuum on the esophagus inner wall at different locations peripherally and longitudinally over time, thus diminishing or preventing damage to the esophagus tissue facing the suction ports.

In one embodiment, each of vacuum lumens 116 is associated with a different valve. In another embodiment, each valve is associated with a set of vacuum lumens 116 that are disposed with sealing portions located at a specific longitudinal location along NGT 102, and controller 110 may controls a location of a sealing of the esophagus against NGT 102 by selecting to activate the valve associated with that location.

Controller 110 and switch 112 may control valve 22 to switch the vacuum between one or more vacuum lumens 116. Valve 22 may be separately connected to each vacuum lumen 116 or may connect to a set of vacuum lumens 116 having suction ports 26 at the same longitudinal location with respect to NGT 102. Hence, controller 110 may signal to activate valve 22 via switch 112 to apply a suction after a time duration from one set of vacuum lumens located at one peripheral and longitudinal location to another set of vacuum lumens located at a different peripheral and/or longitudinal location. Controller 110 may perform such as switch gradually in order to keep the esophagus sealed at least to some extent against NGT 102 during the switch.

NGT 102 may include two or more vacuum lumens 116 which peripherally surround main lumen 108. At least two of vacuum ports 26 are located at different longitudinal locations along NGT 102 in order to allow a longitudinal location switch within the esophagus.

Suction ports 26 may be elliptical, or alternatively, circular. Suction ports 26 may include a graduated edging 28 to prevent or diminish damage to the esophagus tissue while an inner wall of the esophagus is pressed against suction ports 26. Graduated edging 28 is advantageously graduated in an obtuse angle. Graduated edging 28 may be graduated entirely or only include a graduated portion. Generally, graduated edging 28 may provide each of suction ports 26 with a concave shape, having an opening approximately in its middle.

Figure 3:
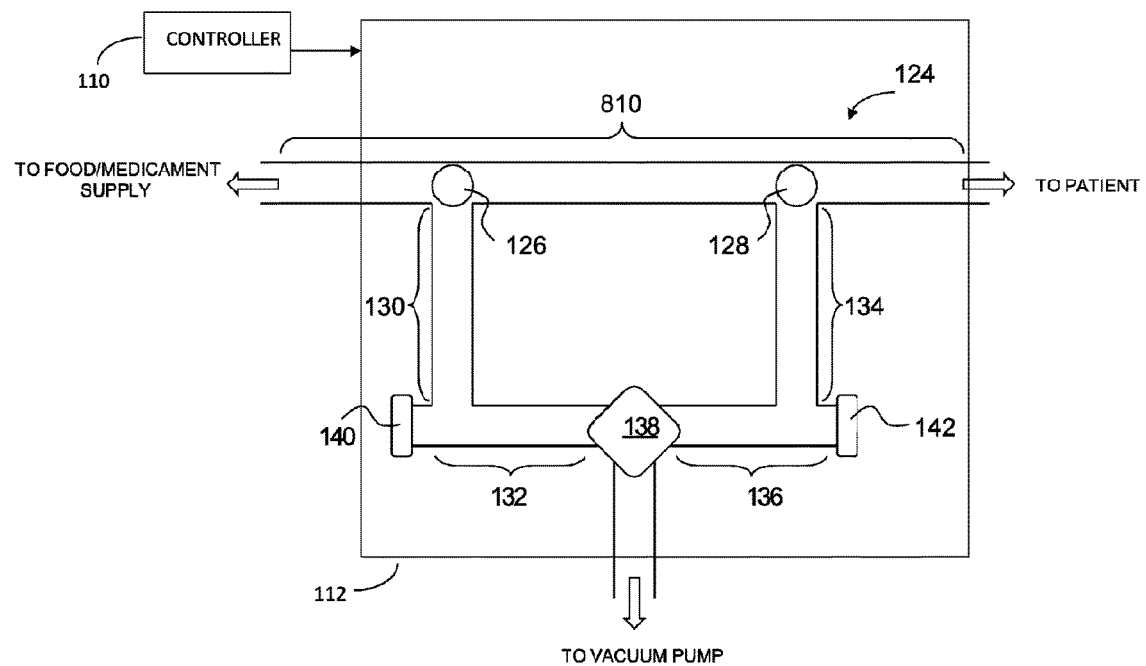
FIG. 3 illustrates a schematic diagram of a manifold included with a switching mechanism.

Reference is now made to FIG. 3, which shows a schematic diagram of a manifold 124 included within switch 112 and which may correspond to valve 22 of FIG. 1. Manifold 124 may be used to interconnect tubes extending between the patient, the food and/or medicament supply, and the vacuum source (e.g. a vacuum pump) and may be included within switch 112.

Main tube 108 may extend between the patient and the food and/or medicament supply (indicated by curly bracket 810). Main tube 108 may include, at manifold 124, two or more junctions 126 and 128. Junctions 126 and 128 may be used by controller 110 to alternate between different vacuum lumens or groups of vacuum lumens. That is, each of junctions 126 and 128 may interconnect different vacuum lumens or groups of vacuum lumens to the vacuum source. Junction 126, for example, may be connected to the vacuum source via a first tube (represented by tube portions 130 and 132). Junction 128, for example, may be connected to the vacuum source via a second tube (represented by tube portions 134 and 136. Tube portions 132 and 136 may be connected to the vacuum source 114 through a selector 138. Selector 138 may have two possible states: In the first state, negative pressure from the vacuum source is channeled towards portion 132 and from there to junction 126. In the second state, negative pressure from the vacuum source is channeled towards portion 136 and from there to junction 128. In embodiments where more than two junctions are present (not shown), a selector may have a number of states corresponding to the number of junctions.

Optionally, controller 110 may control one or more vacuum discharge ports included with manifold 124 for releasing negative pressure from one or more vacuum lumens after the negative pressure has been switched by selector 138. Two exemplary vacuum discharge ports 118 and 120 are shown in the figure. Optionally, the vacuum discharge ports 140 and 142 may each be a cap threadable at some point between selector 138 and junctions 126 and 128, respectively. After the controller 110 has switched the vacuum from a first set of vacuum lumens to a second set of vacuum lumens, the corresponding one of vacuum discharge ports 142 and 142 may be selected to immediately discharge the negative pressure from the set of first vacuum lumens to immediately release the inner wall of the esophagus at the vacuum ports of the first vacuum lumen set to prevent or mitigate tissue damage.

One method of using NGT 102 of the present invention includes the following steps, without limitation and not necessarily in sequential order:
  a) introducing NGT 102 into the esophagus of the subject;
  b) applying vacuum, via controller 110, to one or more of the vacuum sealing portion(s) 24;
  c) adjusting the vacuum level, via controller 110; and
  d) after achieving a desired sealing of the esophagus wall to NGT 10, changing, via controller 110, the vacuum intervals between the vacuum lumens 116 such that NGT 102 remains intact to the esophagus.
  e) applying, via controller 110, a suction to one or more of vacuum lumen 116 which include decompression port(s) 23.

In one embodiment, controller 110 may control the location at which the esophagus couples to NGT 102 over time, in order to diminish tissue damage, by alternately selecting to activate suction within different vacuum lumens that have suction ports at different locations along the length of NGT 102.

In one embodiment, NGT 102 may be provided along the longitudinal axis of the tube with one or more radiopaque stripes that are visible using X-ray imaging and/or other types of electromagnetic radiation imaging. The stripes may be made of any suitable material, such as Barium sulfate at densities of between 40-60%, between 60-80% or higher.

The stripes may endow NGT 102 with a certain rigidity that may assist a caregiver in pushing the tube down the GI tract (or any other bodily lumen), while allowing the tube to resiliently maneuver through the pertinent bodily lumen.

In some embodiments, NGT 102 may administer nutrients or drugs directly to a subject's stomach or intestines and simultaneously or interchangeably enable gastric decompression. Controller 110 may control, coordinate, and synchronize a feeding mechanism, a suction mechanism configured to sealingly draw an inner wall of an esophagus thereagainst, and a gastric decompression mechanism.

In some embodiments, the gastric decompression mechanism comprises one or more vacuum lumens 116 each with a gastric decompression port disposed at a distal end of the vacuum lumen.

In some embodiments, the suction mechanism, controllable by controller 110, is further configured to aspirate fluids from the esophagus. The suction mechanism and the gastric decompression mechanism are, in some embodiments, disposed (situated) and associated by one or more same lumens. In other embodiments, the suction mechanism and the gastric decompression mechanism are configured to perform by independent lumens.

According to some embodiments, controller 110 may control the aspiration of fluids, such as gastric reflux from the esophagus, via any of vacuum lumens 116. In some embodiments, said at least one suction port is configured to aspirate fluids from the esophagus. By virtue of applying a suction via controller 110 and switch 112 to the peripheral lumens of the NGT described herein, the at least one suction port is used for sealingly drawing an inner wall of an esophagus thereagainst and interchangeably or simultaneously aspirate fluids from the esophagus.

Figure 4A:
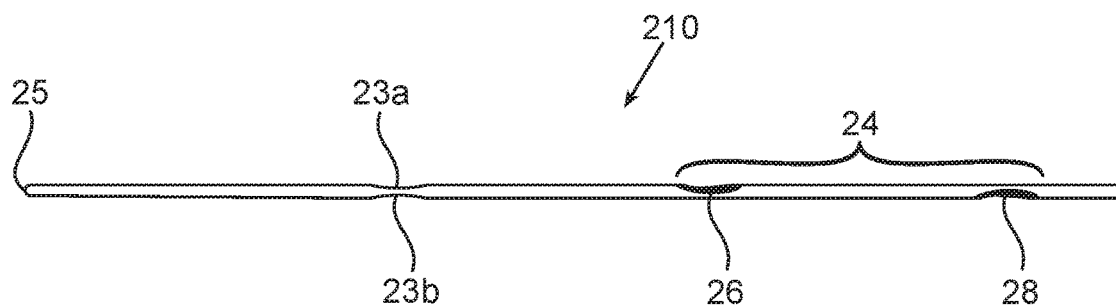
FIGS. 4A-B illustrate a simplified, schematic illustration of a portion of a nasogastric tube, in accordance with an embodiment of the invention.
Figure 4B:
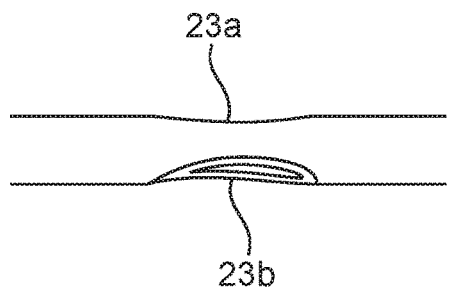

Reference is now made to FIGS. 4A-B. FIG. 4A illustrates a simplified, schematic illustration of a portion 210 of an NGT 102, constructed and operative in accordance with a non-limiting embodiment of the present invention. FIG. 4B is a simplified and enlarged illustration of a distal portion of NGT 102 comprising one or more gastric decompression ports. NGT 102 includes, for example, a vacuum sealing portion 24 comprising two suction ports 28 and 26 distributed between two different locations along the length of NGT 102. NGT 102 further includes one or more gastric decompression ports 23a and 23b disposed distally to the vacuum sealing portion 24. Typically, the one or more gastric decompression ports 23 a and 23 b are configured to be positioned inside a stomach and/or a proximal duodenum.

Generally, without limitation, the distance between one or more gastric decompression ports 23 to at least one suction port is in the range of 50 to 200 mm.

The one or more gastric decompression port(s) 23 is associated with at least one of vacuum lumen 16 (not shown). In some embodiments, the one or more gastric decompression port(s) 23 is associated with a vacuum lumen 116 which comprises one or more suction ports 26. In other embodiments, the one or more gastric decompression port(s) 23 is associated with at least one additional vacuum lumen 116 (such as a vacuum lumen 16 devoid of suction ports 26). Gastric decompression port(s) 23 may be configured to be positioned inside a stomach. Gastric decompression port(s) 23, in another embodiment, may be configured to be positioned inside a proximal duodenum. Gastric decompression port 23 is, in some embodiments, disposed distally to vacuum sealing portion 24 (and suction ports 28 and 26). Decompression port(s) 23 may be elliptical or of any other form, such as circular.

NGT 102 further includes one or more feeding port 25 at the distal end of main lumen 12. In additional embodiments, such as for simultaneous feeding and decompression, the one or more feeding ports 25 are distal to the one or more gastric decompression ports 23. Feeding port 25 may be configured to be positioned in the stomach or in the duodenum. Generally, without limitation, the distance between one or more gastric decompression ports 23 to at least one feeding port is in the range of 50 to 300 mm, or in the range of 100 to 200 mm.

In one embodiment, the one or more gastric decompression port(s) 23 are configured to be positioned in a position selected from a distal esophagus (i.e., distal to vacuum sealing portion 24), inside a stomach, proximal duodenum, or a combination thereof. In embodiments wherein gastric decompression port(s) 23 are configured to be positioned in the proximal duodenum, feeding port 25 may be configured to be positioned in a distal duodenum.

Vacuum lumen 116 comprising a decompression port 23 may be constructed of similar materials to vacuum lumen 116 comprising suction ports 26, but alternatively may be constructed of medically safe metals, such as but not limited to, stainless steel, titanium alloys, NITINOL and others.

As known to one skilled in the art, the system described herein may further comprise a guiding probe (e.g., a stylet) for inserting NGT 102 into a subject. The guiding probe is typically is removed after confirming the correct placement of NGT 102.

A method of using NGT 102 of the present invention may include the following steps, without limitation and not necessarily in sequential order:

a) introducing NGT 102 into an esophagus of a patient;
b) applying a suction, via controller 110 and switch 112, to one or more decompression ports; and
c) applying a suction, via controller 110 and switch 112, to one or more suction ports interchangeably between the differently located suction ports so as to sealingly draw an inner wall of the esophagus thereagainst each time in a different location along the esophagus.

In some embodiments, controller 110 may provide a user interface allowing a practitioner to define the timing and vacuum pressure settings disclosed herein for any of lumens 116. Alternatively, controller 110 may receive the timing and vacuum pressure settings via any suitable means, such as wired, or wireless communication, USB, CD-ROM or the like.

The suction may be applied, via controller 110 and switch 112, to vacuum lumen(s) in a constant manner or alternatively in timely intervals. As such, suction may be applied to the decompression ports to, during or after a patient is being fed by the NGT described herein. In additional embodiments, vacuum may be applied to the decompression ports according to the subject request, such as in result to abdominal discomfort, including but not limited to, excessive gastric gas or the like.

The vacuum may be applied to one or more vacuum lumens each time, and in each time to vacuum lumens which include suction ports peripherally distributed around the same location along a longitudinal axis of NGT 102 or peripherally distributed around different locations along a longitudinal axis of NGT 102.

The interchanging between the vacuum lumens to which a vacuum is applied may be performed at various manners, for example, it may be performed once or more per patient while each location change may be performed once in a constant or variable period of time, all according to the caregiver discretion regarding the specific patient.

In some embodiments, said vacuum is applied to one or more suction ports interchangeably between the differently located suction ports so as to sealingly draw an inner wall of the esophagus thereagainst each time in a different location along the esophagus.

The method may further include the step of regulating the vacuum so that a suction level is not constant over time in the suction ports. The vacuum may be regulated to the vacuum ports so as to create peristaltic movement or other oscillatory movement of the esophagus.

In some embodiments, the vacuum may be applied such that to restricts at least 60% of passage through the esophagus.

In some embodiments of the present invention, NGT 102 may be used to insert one or more probes through main lumen 108, through one or more of vacuum lumens 116 and/or through a different, dedicated lumen (not shown) into the patient's body. Such probes may include, for example: a temperature sensor, an electromagnetic radiation sensor, a pH sensor, an image sensor, a fiber optic, an ultrasound probe, an OCT (optical coherence tomography) probe, a mini MRI (magnetic resonance imaging) probe, etc.

Figure 5A:
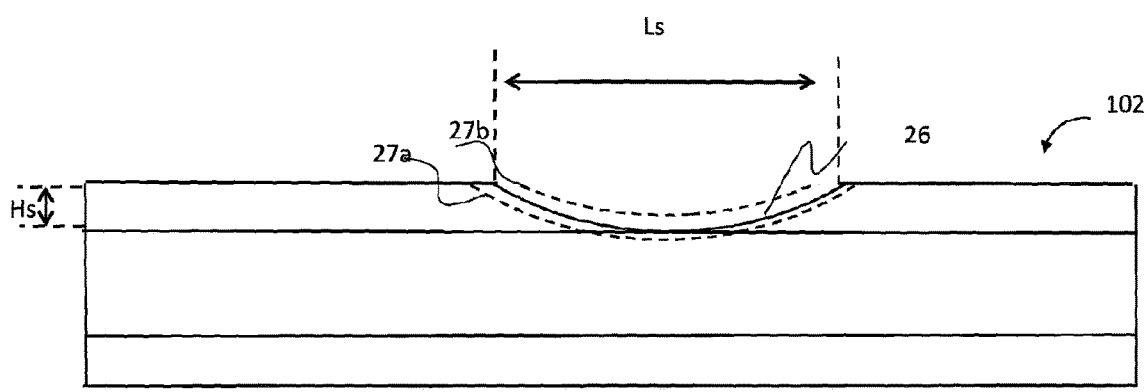
FIGS. 5A-B depicting a longitudinal section of a nasogastric tube, in accordance with an embodiment of the invention.
Figure 5B:
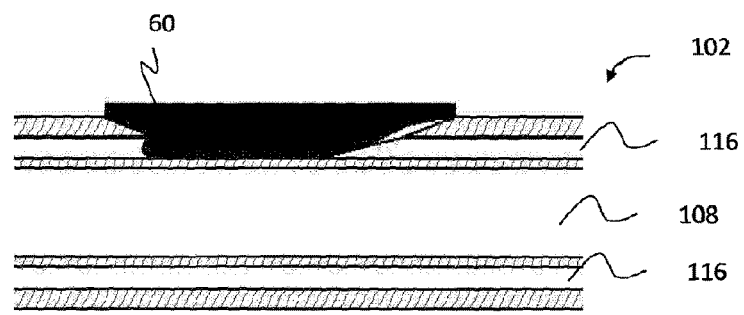

Reference is made to FIGS. 5A-B depicting a longitudinal section of an embodiment of NGT 102, having a main lumen and one vacuum lumen comprising a suction unit (or suction port). For simplicity of discussion, only one suction port is shown while it should be appreciated that more than one suction port may be included. FIG. 8B further depicts a tissue, e.g., esophagus tissue, being pulled in by the applied vacuum force. It will be appreciated by a person skilled in the art that in order to couple the tissue to the tube, the tissue should reach the lumen base. Nevertheless, clinical trials have shown tissue damage in cases when the applied vacuum sucked the tissue into the vacuum lumen (i.e., beyond the suction port). Thus, the NGT described herein provides specific and unique structure of one or more suction ports and/or of the vacuum lumen which substantially prevent tissue damage.

In some embodiments, a nasogastric tube of the invention comprises at least one vacuum lumen comprising at least one suction port for sealingly drawing an inner wall of an esophagus thereagainst, said at least one suction port has a concavity whose longitudinal cross-section has a shape delimited between (i) a first arc of a first circle, the first arc having a length of 25 millimeters and a height of 1.5 millimeters, and (ii) a second arc of a second circle, the second arc having a length of 15 millimeters and a height of 1 millimeter.

Reference is now made to FIG. 5A. FIG. 5A is a simplified, schematic illustration of a side view of a portion of a nasogastric tube, constructed and operative in accordance with a non-limiting embodiment of the present invention. For simplicity only, one suction port 26 is shown. NGT 102 comprises suction port(s) 26 having a concavity whose longitudinal cross-section has a shape delimited between a first arc of a first circle 27a and a second arc of a second circle 27b.

In some embodiments, the first arc of a first circle has a length of 25 millimeters and a height of 1.5 millimeters. In some embodiments, said first arc of a first circle has a length of 24 millimeters, 23 millimeters, 22 millimeters or 21 millimeters and a height of 1.5 millimeters. In another embodiment, said first arc of a first circle has a length of 25 millimeters, 24 millimeters, 23 millimeters, 22 millimeters or 21 millimeters and a height of 1.4 millimeters. In another embodiment, said first arc of a first circle has a length of 25 millimeters, 24 millimeters, 23 millimeters, 22 millimeters or 21 millimeters and a height of 1.3 millimeters. In another embodiment, said first arc of a first circle has a length of 25 millimeters, 24 millimeters, 23 millimeters, 22 millimeters or 21 millimeters and a height of 1 millimeters.

In another embodiment, the second arc of a second circle has a length of 15 millimeters and a height of 1 millimeter. In another embodiment, said second arc of a second circle has a length of 15 millimeters, 16 millimeters, 17 millimeters, 18 millimeters, 19 millimeters or 20 millimeters and a height of 1 millimeters. In another embodiment, said second arc of a second circle has a length of 15 millimeters, 16 millimeters, 17 millimeters, 18 millimeters, 19 millimeters or 20 millimeters and a height of 1.1 millimeters. In another embodiment, said second arc of a second circle has a length of 15 millimeters, 16 millimeters, 17 millimeters, 18 millimeters, 19 millimeters or 20 millimeters and a height of 1.2 millimeters.

In another embodiment, the at least one suction port 26 has a concavity having an arc having a length of 18 mm, 19 mm, 20 mm, 21 mm or 22 mm, wherein each possibility represents a separate embodiment of the present invention. In exemplary embodiments, said arc has a length between 20 mm-21 mm, 20.1 mm, 20.3 mm or approximately 20.12 mm.

Said concavity of said suction port may alternatively be defined by a height Hs and Ls as depicted in FIG. 5A. In some embodiments, the one or more suction ports have a maximum concavity Hs of 1.5 mm as measured over a length Ls of 20 mm. In some embodiments, the one or more suction ports have a maximum concavity Hs of 1.4 mm as measured over a length Ls of 20 mm. In some embodiments, the one or more suction ports have a maximum concavity Hs of 1.3 mm as measured over a length Ls of 20 mm. In some embodiments, the one or more suction ports have a maximum concavity Hs of 1.2 mm as measured over a length Ls of 20 mm. In another embodiment, said length Ls is 18 mm, 19 mm, 20 mm, 21 mm or 22 mm, wherein each possibility represents a separate embodiment of the present invention.

Reference is made to FIG. 5B depicting a transparent longitudinal section of an embodiment of an NGT of the invention. NGT 102 comprises a main lumen 108 and one or more vacuum lumen(s) 116 comprising a suction port. When negative pressure is applied (i.e. vacuum), tissue 60 (e.g., esophagus tissue), is pulled in to the suction port. FIG. 5B shows as a non-limiting embodiment a cause for issue damage in cases when the applied vacuum sucks the tissue into the vacuum lumen 16 (i.e., beyond the suction port). In some embodiments, NGT 102 described herein provides specific and unique structure of one or more suction ports and/or of the vacuum lumen 26 which substantially prevent drawing of tissue in to the vacuum lumen 116 and thus prevent tissue damage.

Suction ports 26 are in some embodiments substantially rectangular shaped, and may have rounded corners. In other embodiments, suction ports 26 are elliptical or circular.

In some embodiments, at least one suction port 26 may include two or more suction ports, successively arranged along a portion of a longitudinal axis of NGT 102.

Figure 6A:
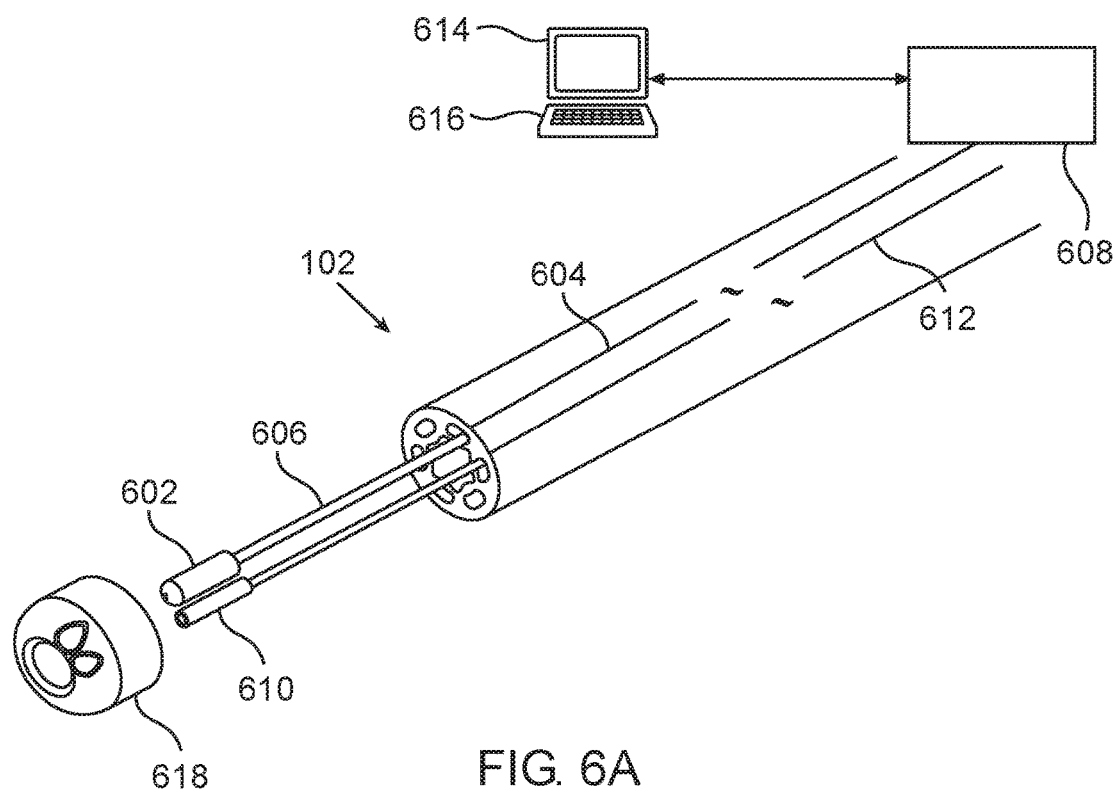
FIGS. 6A-B illustrate an imaging system provided with a nasogastric tube, in accordance with an embodiment of the invention.
Figure 6B:
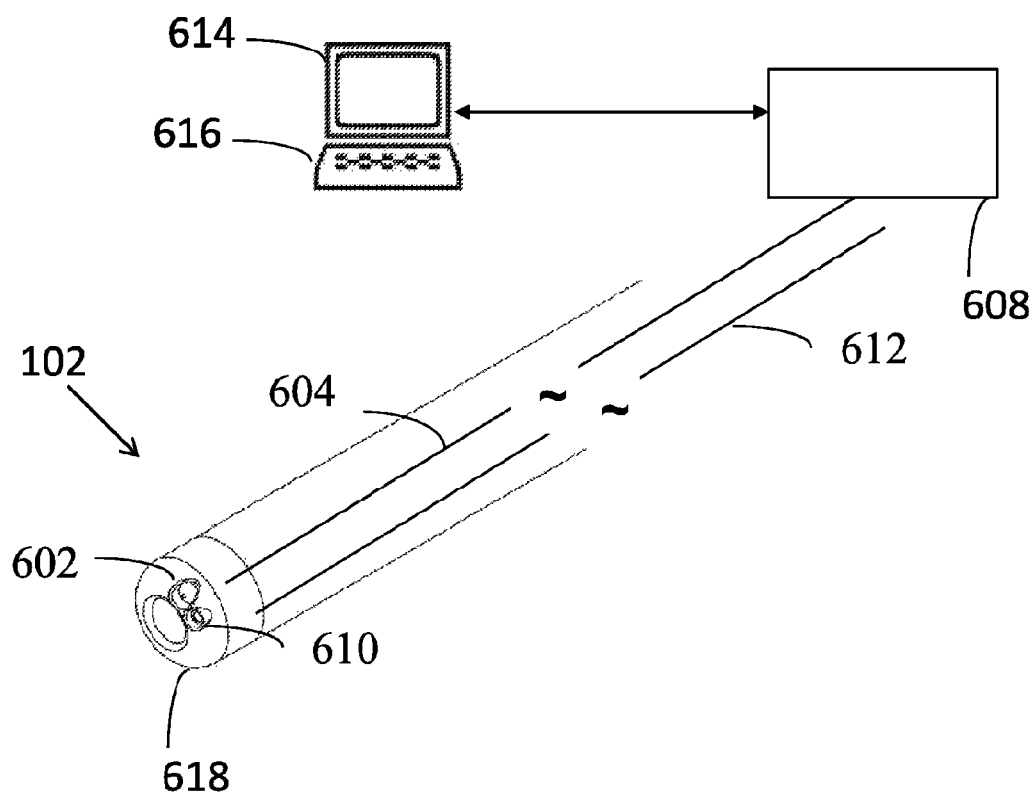

Reference is now made to FIGS. 6A-B which illustrate an imaging system provided with NGT 102 for capturing and rendering one or more images of an area accessible by NGT 102. The distal end of NGT 102 may be provided with a camera 602 and an orientation adjustor disposed at a distal end of NGT 102, as well as a camera cable 604 connecting camera 602 and orientation adjustor 606 to a processing unit 608 disposed at a proximal end of NGT 102. Camera 602 may include one or more optical lenses mounted to a sensor, such as a complementary metal-oxide semiconductor (CMOS) or charged coupled device (CCD) sensor, and may capture one or more images of an area accessible by NGT 10, such as the esophagus, stomach and/or intestines. Images captured by camera 602 may be communicated to video processing unit 608 via camera cable 604. Camera cable 604 may additionally provide power and a control signal from processing unit 608 to any of camera 602 and orientation adjustor 606.

Imaging system 600 may provide an illuminator 610, such as one or more LED light sources or fiber-optic light source, at a distal end of NGT 102 to illuminate an area surrounding the camera 602, enabling camera 602 to capture the images. Illuminator 610 may powered and controlled by processing unit 608 via a light cable 612 connecting illuminator 610 to processing unit 608.

In an embodiment, camera 602 and illuminator 610 may be sealed to prevent damage from inner bodily fluids.

Camera 602 and/or illuminator 610 may be affixed to NGT 102 via any suitable means, such as via an adhesive to an exterior side of NGT 102, or within any lumens provided with NGT 102. In one embodiment, camera 602 and/or illuminator 610 may be affixed to the distal end of NGT 102 via a threaded connection, mechanical clip or spring joint, allowing for easy attachment, detachment, or replacement. Camera cable 604 and light cable 612 may be housed in one or more lumens provided with NGT 102, such as any of the vacuum lumens provided with NGT 102, or in main lumen

108, in a manner to isolate the cables from any bodily fluids present in or around NGT 102 to prevent their becoming wet or otherwise damaged. Alternatively the cables may be insulated and affixed externally to NGT 102. Camera cable 602 and light cable 612 may be isolated from each other to reduce noise. Camera cable 602 and/or light cable 612 may be compatible with any suitable communications protocol, such as RS232 protocol, USB, RS-422, firewire, camera link, or gigabit Ethernet protocol communication line, to name a few.

Video processing unit 608 may be disposed at a proximal end of NGT 102 and may transmit via any of camera cable 602 and light cable 612 a control signal to control features such automatic gain control (AGC), exposure control, on/off switch, and/or color balance for imaging unit 602 and/or illuminator 610. In one embodiment, video processing unit 608 may enable controlling the orientation of camera 602 with a control signal transmitted via camera cable 604 to orientation adjustor 606, to enable capturing images from different angles within the esophagus, stomach and/or intestines.

Video processing unit 608 may receive and store the captured images via camera cable 604, and process and render the images. A display screen 614 may be provided with video processing unit 606 to display or otherwise render the images captured by camera 602 for viewing by a user. The user may apply one or more control signals, via a control panel 616 provided with video processing unit 608, to control any of camera 602 and/or illuminator 610 in response to the images displayed on display screen 614.

In another embodiment a work channel may be disposed with nasogastric tube 102 to provide a tool to an area accessible by NGT 102, such as for removing a blockage detected by camera 602.

In another embodiment, an irrigation lumen may be disposed with NGT 102 to irrigate a blocked region that is accessible by NGT 102.

A cap 618 may provided at the distal end of NGT 102 to enclose and insulate any of the components of imaging system 600. Cap 618 may be disposed with an opening for camera 602, another opening for illuminator 610, and at least a third opening for any of a feeding tube and/or vacuum lumens provided with NGT 102.

A method for inserting NGT 102 of the present invention may include the following steps, without limitation and not necessarily in sequential order:
the distal end of NGT 102 may be introduced into the esophagus of the patient by an operator;
one or more images of an area illuminated by the illuminator may be captured by the camera;
the captured images may be transmitted to a processing unit;
the processed images may be rendered on a display unit;
the operator may monitor the progress of the distal end of the tube via the rendered images;
the operator may adjust the positioning of the tube in response to the rendered images;
the operator may adjust the orientation of the camera in response to the rendered images;
the operator may adjust the intensity of the illuminator in response to the rendered image.

The present invention may be a system, a method, and/or a computer program product. The computer program product may include a computer readable storage medium (or media) having computer readable program instructions thereon for causing a processor to carry out aspects of the present invention.

The computer readable storage medium can be a non-transitory, tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention may be described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

The invention claimed is:

1. An enteral feeding system comprising:
an enteral feeding tube comprising:
(a) a main lumen having one or more proximal connectors for connecting to a source of substances or pressure;
(b) at least four discrete vacuum lumens peripherally surrounding said main lumen; each said at least four vacuum lumens comprising a suction port for sealingly drawing an inner wall of an esophagus thereagainst, wherein at least some of said suction ports are spaced apart between at least two different locations along a longitudinal axis of said tube; and
(c) an electronically controlled switching mechanism comprising one or more suction valves connected to said at least four vacuum lumens, said one or more suction valves are structured to interchange applied vacuum between those of said at least four vacuum lumens which are associated with suction ports located at a first longitudinal location and those of said at least four vacuum lumens which are associated with suction ports located at a second longitudinal location, thereby changing location of esophagus sealing to the enteral feeding tube and diminishing or preventing damage to esophageal tissue caused by applying suction;
a pump configured to draw a liquid from a reservoir to the enteral feeding tube; and
a controller configured to automatically control the pump and the switching mechanism and to prevent said pump from providing a liquid to said main lumen unless the esophagus of the patient is sealingly drawn against at least some of the suction ports of the at least four vacuum lumens,
wherein controlling the pump and the switching mechanism comprises coordinating the operation of the switching mechanism with the operation of the pump, thereby coordinating the changing of the location of esophagus sealing to the enteral feeding tube with supply of the liquid.

2. The apparatus of claim 1, wherein the controller is configured to control the switching mechanism by selecting to activate or deactivate any of the one or more suction valves.

3. The apparatus of claim 2, wherein each of the at least four vacuum lumens is associated with a different valve of the one or more valves.

4. The apparatus of claim 1, wherein the one or more suction valves are selected from the group consisting of: a pinch valve, a butterfly valve, and a diaphragm valve.

5. The apparatus of claim 1, wherein the controller is configured to alternate suction between the vacuum lumens having suction ports at a distal location and the vacuum lumens having suction ports at a proximal location of the enteral feeding tube.

6. The apparatus of claim 1, further comprising a decompression lumen comprising a decompression port positioned distally to the suction ports of the at least four vacuum ports and a gastric decompression valve; wherein the controller is further configured to control said gastric decompression valve via said switching mechanism.

7. The apparatus of claim 6, wherein the gastric decompression lumen is configured to siphon a fluid from a stomach of a patient to the reservoir coupled to the decompression lumen via the switching mechanism.

8. The apparatus of claim 1, further comprising a user interface to enable a practitioner to set one or more parameters for controlling application of a suction to any of the two or more lumens via the controller and switching mechanism.

9. The apparatus of claim 8, further comprising a second user interface to enable a patient to set a subset of the one or more parameters.

10. The apparatus of claim 9, wherein the user interface may enable the practitioner and/or patient to instruct the controller to activate the decompression valve to relieve abdominal discomfort.

11. The apparatus of claim 1, wherein the decompression port is positioned 50-200 mm distally to the suction ports of the at least four vacuum lumens.

12. The apparatus of claim 1, wherein the controller is configured to control the suction applied for a predetermined time period after said pump has finished delivering food and/or medicine via said main lumen.

13. The apparatus of claim 1, wherein the controller is configured to control flow through the decompression lumen and coordinate it with the operation of the pump and/or the suction valve.

14. A method for enteral feeding, comprising:
  controlling an operation of a pump to draw a liquid from a reservoir to an enteral feeding tube that is inserted into an esophagus of a patient; and
  controlling an operation of a switch associated with at least four vacuum lumens provided with the enteral feeding tube, thereby providing the liquid to the patient's stomach via the enteral feeding tube, while providing a vacuum to at least two of the at least four vacuum lumens, thereby sealing the wall of the esophagus to the at least four vacuum lumens; wherein controlling the operation of the switch comprises:
    interchanging the applied vacuum between the vacuum lumens associated with suction ports located at a first longitudinal location and the vacuum lumens associated with suction ports located at a second longitudinal location, thereby changing sealing location of the esophagus to the enteral feeding tube;
    coordinating the operation of the switch with the operation of the pump, thereby coordinating the changing of the sealing location of the sealing to the enteral feeding tube with supply of the liquid; and
    controlling operation of the pump so as to prevent liquid from being provided to the tube unless the esophagus of the patient is sealingly drawn thereagainst.

15. The method of claim 14, further comprising decompressing the patient's stomach or intestine via a gastric decompression lumen provided with the enteral feeding tube.

16. The method of claim 14, wherein controlling the switch comprises applying suction for a predetermined time period after the pump has finished delivering food and/or medicine via the tube.

* * * * *